US011266680B2

(12) United States Patent
Salome et al.

(10) Patent No.: US 11,266,680 B2
(45) Date of Patent: Mar. 8, 2022

(54) COMPOSITIONS BASED ON METHYL CYCLODEXTRINS FOR THE TREATMENT AND/OR PREVENTION OF DISEASES BY INCREASING THE HDL CHOLESTEROL LEVEL

(71) Applicant: Roquette Freres, Lestrem (FR)

(72) Inventors: Marc Salome, Mervilla (FR); Daniel Wils, Morbecque (FR); Xavier Parissaux, Saint Omer (FR); Francois Mach, Geneva (CH); Fabrizio Montecucco, Geneva (CH)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 15/903,738

(22) Filed: Feb. 23, 2018

(65) Prior Publication Data

US 2018/0207198 A1    Jul. 26, 2018

Related U.S. Application Data

(62) Division of application No. 15/039,864, filed as application No. PCT/FR2014/053309 on Dec. 12, 2014, now Pat. No. 10,022,392.

(30) Foreign Application Priority Data

Dec. 13, 2013    (FR) .................... 1362633

(51) Int. Cl.
    *A61K 31/724*    (2006.01)
    *A61K 45/06*    (2006.01)

(52) U.S. Cl.
    CPC ............ *A61K 31/724* (2013.01); *A61K 45/06* (2013.01)

(58) Field of Classification Search
    CPC ............................. A61K 31/724; A61K 45/06
    See application file for complete search history.

(56) References Cited

U.S. PATENT DOCUMENTS

| 7,456,275 | B2 | 11/2008 | Shimoboji |
| 2004/0259853 | A1 | 12/2004 | Tabas |
| 2006/0040894 | A1 | 2/2006 | Hunter et al. |
| 2008/0025970 | A1 | 1/2008 | Poston |
| 2008/0032925 | A1 | 2/2008 | Hauser |
| 2013/0196947 | A1 | 8/2013 | Cataldo et al. |

FOREIGN PATENT DOCUMENTS

| JP | S62265230 A | 11/1987 |
| WO | 1994022461 A1 | 10/1994 |
| WO | 9938498 A1 | 8/1999 |
| WO | WO-0243742 A1 | 6/2002 |
| WO | 2003097045 A1 | 11/2003 |
| WO | 2006037769 A1 | 4/2006 |

OTHER PUBLICATIONS

Davidson et al., PLoS ONE, 2009, 4(9), e6951, p. 1-15. (Year: 2009).*
Jacquet et al., Journal of Chromatography A, 2005, 1083, p. 106-112. (Year: 2005).*
Schonbeck et al., Langmuir, 2011,27, p. 5832-5841. (Year: 2011).*
Xu et al., J. Biol. Chem., 2012, 287(47), p. 39349-39360. (Year: 2012).*
Busseuil et al., "A Study fo the Effect of Methyl-β-Cyclodextrin on Cholesterol Content and Vascular Responses of the Porcine Isolated Coronary Artery," British Journal of Pharmacology, 2000, p. 10P, vol. 131, No. Proc. Sup., XP-002726511.
Castagne et al., "Spectroscopic Studies and Molecular Modeling for Understanding the Interactions Between Cholesterol and Cyclodextrins," J. Pharm. Pharmceut. Sci., 2010, 13(2), p. 362-377.
Dass et al., "Apolipoprotein A-I, Cyclodextrins and Liposomes as Potential Drugs for the Reversal of Atherosclerosis. A Review," J. Pharm. Pharmacol., 2000, 52, pp. 731-761.
Kiss et al., "Evaluation of cytotoxicity of β-cyclodextrin derivatives: Evidence for the role of cholesterol extraction," Eur. J. Pharm. Sci., 2010, 40, p. 376-380.
O'Keefe et al., "Should an Angiotensin-Converting Enzyme Inhibitor Be Standard Therapy for Patients with Atherosclerotic Disease?" J. Am. Coll. Cardiol., 2001, 37 (1), pp. 1-8.
Swaroop et al., "Evaluation of Cholesterol Reduction Activity of Methyl-b-Cyclodextrin Using Differentiated Human Neurons and Astrocytes," Journal of Biomolecular Screening, 2012, pp. 1243-1252, vol. 17, No. 9.
Trautwein et al., "Impact of β-cyclodextrin and resistant starch on bile acid metabolism and fecal steroid excretion in regard to their hypolipidemic action in hamsters," Biochimica et Biophysica Acta, 1999, 1437, p. 1-12.
Written Opinion in Internatinoal Application No. PCT/FR2014/053309, dated Mar. 20, 2015, pp. 1-7.
The European Search Report, dated Nov. 13, 2019, in the related European Appl. No. 2019184268.
The English translation of the Russian Office Action, dated Jul. 4, 2018, in the related Russian Appl. No. 2016128411.
The English translation of the Japanese Office Action, dated Jan. 23, 2019, in the related Japanese Appl. No. 2018-073664.
The English translation of the Japanese Office Action, dated Apr. 26, 2017, in the related Japanese Appl. No. 2016-538683.
Pazit Bar-On et al.: "Effects of the cholesterol-lowering compound methyl-[beta]-cyclodextrin in models of [alpha]-synucleinopathy", Journal of Neurochemistry, vol. 98, No. 4, Aug. 1, 2006, pp. 1032-1045, XP55548018.
Ohm et al., "Cholesterol, statins and tau," Acta Neurol Scand, 2006, vol. 114, Suppl. 185, pp. 93-101.

(Continued)

*Primary Examiner* — Jonathan S Lau

(57) ABSTRACT

Pharmaceutical composition and their uses are disclosed, the composition comprising at least one methyl cyclodextrin having a molar substitution (MS) degree of between 0.05 and 1.5 in the treatment and/or prevention of diseases that can be treated and/or prevented by an increase in the HDL cholesterol level.

20 Claims, 2 Drawing Sheets

Figure 1:
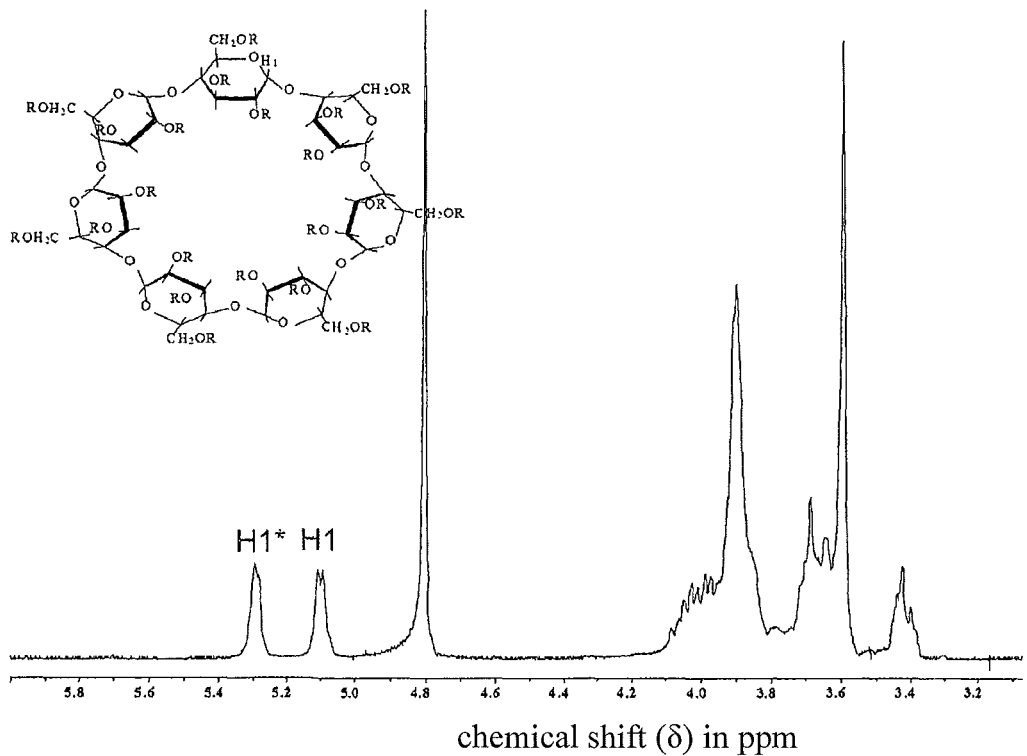

Specification includes a Sequence Listing.

(56) References Cited

OTHER PUBLICATIONS

Madra et al., "Niemann-Pick type C pathogenesis and treatment: from statins to sugars," Clinical Lipidology, 2010, vol. 5, No. 3, pp. 387-395.

Vyas, "Preparation, characterization and pharmacodynamic activity of supramolecular and colloidal systems of rosuvastatin-cyclodextrin complexes," J. Incl. Phenom Macrocycl. Chern., Jun. 9, 2012, 76(1-2), pp. 37-46.

* cited by examiner

SEQUENCE LISTING

<160> NUMBER OF SEQ ID NOS: 6

<210> SEQ ID NO 1
<211> LENGTH: 19
<212> TYPE: DNA
<213> ORGANISM: artificial sequence
<220> FEATURE:
<223> OTHER INFORMATION: primer

<400> SEQUENCE: 1
gtgtctcgcc tgttctcag                                                    19

<210> SEQ ID NO 2
<211> LENGTH: 19
<212> TYPE: DNA
<213> ORGANISM: artificial sequence
<220> FEATURE:
<223> OTHER INFORMATION: primer

<400> SEQUENCE: 2
gaaacatcac ctcctgccg                                                    19

<210> SEQ ID NO 3
<211> LENGTH: 22
<212> TYPE: DNA
<213> ORGANISM: artificial sequence
<220> FEATURE:
<223> OTHER INFORMATION: primer

<400> SEQUENCE: 3
gaggaagaaa ggatacaaga cc                                                22

<210> SEQ ID NO 4
<211> LENGTH: 22
<212> TYPE: DNA
<213> ORGANISM: artificial sequence
<220> FEATURE:
<223> OTHER INFORMATION: primer

<400> SEQUENCE: 4
gtcagtatct ccttgaccat tt                                                22

<210> SEQ ID NO 5
<211> LENGTH: 22
<212> TYPE: DNA
<213> ORGANISM: artificial sequence
<220> FEATURE:
<223> OTHER INFORMATION: primer

<400> SEQUENCE: 5
cccttaatcc acctcatcaa tc                                                22

<210> SEQ ID NO 6
<211> LENGTH: 22
<212> TYPE: DNA
<213> ORGANISM: artificial sequence
<220> FEATURE:
<223> OTHER INFORMATION: primer

<400> SEQUENCE: 6
gaagtttttg acccctgtga ac                                                22

COMPOSITIONS BASED ON METHYL CYCLODEXTRINS FOR THE TREATMENT AND/OR PREVENTION OF DISEASES BY INCREASING THE HDL CHOLESTEROL LEVEL

This application is a divisional of U.S. application Ser. No. 15/039,864, filed May 27, 2016, which is the U.S. national stage application of International Patent Application No. PCT/FR2014/053309, filed Dec. 12, 2014.

SEQUENCE LISTING

The instant application contains a Sequence Listing which has been filed electronically in ASCII format and is hereby incorporated by reference in its entirety. Said ASCII copy, created on Apr. 4, 2018, is named 200588-00259_SL.txt and is 1,524 bytes in size.

The present invention relates to pharmaceutical compositions which make it possible to increase the HDL cholesterol level in an individual. The present invention relates more specifically to the use of a pharmaceutical composition in the treatment and/or prevention of diseases that can be treated and/or prevented by an increase in the HDL cholesterol level, or in the treatment and/or prevention of atherosclerosis or complications relating to an atheroma, or diseases of the central nervous system.

TECHNOLOGICAL BACKGROUND OF THE INVENTION

Cholesterol is a lipid of the sterol family which plays an essential role in numerous biochemical processes.

It is a major component of animal cell membranes which contributes to their stability and to the maintaining of their structure by inserting between the phospholipids. Indeed, cholesterol stiffens the membrane by preventing gelling thereof since it prevents fatty acid crystallization and also decreases membrane permeability to water-soluble molecules. By inserting into membranes, cholesterol also allows the formation of lipid rafts which are areas essential to the anchoring of functional proteins.

Moreover, cholesterol is also found in neurons, where it enables neurotransmitter synthesis by exocytosis and therefore nerve message propagation. It is directly involved in the formation of beta-amyloid peptides, and therefore in the pathogenesis of Alzheimer's disease. An association between atherosclerosis and Alzheimer's disease has also been demonstrated (Mikael Simons and al., "Cholesterol depletion inhibits the generation of b-amyloid in hippocampal neurons", *Proc. Natl. Acad. Sci. USA*; Vol. 95, pp. 6460-6464, May 1998, Neurobiology.)

Cholesterol metabolism is also a precursor of numerous molecules, for instance steroid hormones (cortisol, cortisone and aldosterone), steroid sex hormones (progesterone, estrogens and testosterone), vitamin D3, heme A, prenylated and farnesylated proteins, ubiquinone or coenzyme Q10, dolichol, the nuclear factor NF kappa B, the Tau protein and bile salts.

Cholesterol is carried in the blood by transport systems with very different roles, namely LDL lipoproteins (low-density lipoproteins) and HDL lipoproteins (high-density lipoproteins).

HDL cholesterol is considered to be protective with respect to cardiovascular diseases and is frequently indicated as being "good cholesterol".

Cholesterol-transporting LDLs penetrate into the arterial wall and are then taken up by the monocytes and macrophages residing in this arterial wall and also by the smooth muscle cells. This results in an excessive lipid load in the macrophages and smooth muscle cells which are then converted into foam cells responsible for the processes of atherosclerosis and corresponding to the first stage of atheromatous plaque formation. It is therefore a question of "bad cholesterol".

Atheroma is defined by the World Health Organization as a "variable combination of changes in the intima of large and medium caliber arteries consisting of focal accumulations of lipids, complex carbohydrates, blood and calcium deposits associated with medial changes". Atheroma is responsible for the majority of cardiovascular diseases and is the principal cause of morbidity and mortality in industrialized countries. Atheroma begins with the formation of a "fatty streak", a simple linear deposit of fat with no effect on blood flow, located between the endothelium and media of the artery. Over time, this streak can become bigger, and become loaded with lipids, fibrinogen, platelets and other blood cells, and calcium, so as to constitute the "atheromatous plaque". Said plaque becomes more or less large and can reduce the caliber of the artery sufficiently to reduce its flow rate.

There are two types of complications: the first, which evolves over the long term, is due to its slow growth, increasingly impairing the passage of blood until it completely prevents it by blockage. The second, which is rapid and responsible for the acute complications, consists of damage to or rupture of the endothelium: the breach formed is then blocked by an aggregation of blood platelets and the formation of a blood clot which can rapidly totally block the vessel. This clot can also detach and block further downstream. The plaque can also partially detach and also block the artery, or more rarely, release its content and produce a cholesterol embolism. Finally, the dilation of the arterial wall induced by the increase in volume of the plaque can result in the formation of an aneurysm, with a risk of rupture.

The pharmaceutical class most widely used for preventing atheroma is the statins, which aim to reduce the circulating lipid and LDL cholesterol level, in addition to an appropriate diet. However, the advantage and usefulness of statins has for a while been sharply criticized by some researchers and clinicians who assert that statins, after analysis of controversial since contradictory statistical trials, do not provide patients with the expected therapeutic benefit. Added to this implication are the harmful and even sometimes dramatic side effects which have been identified and have, in certain cases, led to withdrawal from the market.

The other drug treatments proposed today are:
platelet aggregation inhibitors such as aspirin or clopidogrel, which are supposed to decrease the formation of clots from the atheromatous plaque;
antihypertensive drugs, such as angiotensin-converting enzyme inhibitors.

The pharmaceutical treatments which exist at the current time are therefore solely aimed at decreasing the risks associated with atheroma. None of the drugs which exist on the market directly attacks the atheromatous plaque.

When the vital prognosis is brought into play, the treatment is surgical or endovascular. It aims to restore the arterial lumen, to irrigate the oxygen-deprived area or to eliminate the arterial aneurysm. Among these techniques, mention may be made of angioplasty, unblocking by endarterectomy, and bypass.

Finally, the principal means for combating atheroma and complications thereof still remains today behavioral in nature: giving up smoking, developing physical activity, controlling blood pressure, correcting a dyslipidaemia, controlling diabetes, diet.

Thus, it must be noted that there has for a long time clearly been an unsatisfied need for treatment and/or prevention of atheroma.

Various approaches have however been attempted, without it having been possible for a new solution to be retained. HDL cholesterol in particular began to be studied in 1975 when researchers demonstrated the relationship between high HDL cholesterol levels and a decrease in the incidence of cardiovascular diseases (Rye K. A. 2013. High density lipoprotein structure, function, and metabolism: a new Thematic Series. *J Lipid Res.* 54:(8) 2031-2033). The positive results of these studies have encouraged the development of treatments aimed at increasing HDL cholesterol levels, among which inhibitors of the CETP (cholesterol ester transfer protein) enzyme, which were the very first agents developed and evaluated on a large scale, specifically for this purpose, will be retained. However, none of these treatments has made it possible to reduce the occurrence of cardiovascular events.

Finally, there is still no drug available on the market that is capable of effectively inducing an increase in HDL cholesterol level in patients, in particular because the mechanisms involved are still today far from being elucidated. In particular, there is no drug available on the market that is capable of effectively and actively combating diseases that can be treated and/or prevented by an increase in the HDL cholesterol level. In addition, there is a constant need for a drug capable of combating atherosclerosis, in particular atheromatous plaque formation.

SUMMARY OF THE INVENTION

It is to the applicant's credit to have discovered that pharmaceutical compositions based on methyl cyclodextrin having a particular degree of molar substitution of between 0.05 and 1.5 make it possible to induce an increase in the HDL cholesterol level, in particular in the plasma HDL cholesterol level, and are therefore extremely advantageous for the treatment or prevention of diseases that can be treated and/or prevented by an increase in the HDL cholesterol level, in particular of atherosclerosis or complications relating to an atheroma, or diseases of the central nervous system.

The object of the present invention is therefore to provide a pharmaceutical composition comprising at least one methyl cyclodextrin having a degree of molar substitution of between 0.05 and 1.5, for use thereof in the treatment and/or prevention of diseases that can be treated and/or prevented by an increase in the HDL cholesterol level.

Another object of the present invention is to provide a pharmaceutical composition comprising at least one methyl cyclodextrin having a degree of molar substitution of between 0.05 and 1.5, for use thereof in the treatment and/or prevention of atherosclerosis or complications relating to an atheroma, or diseases of the central nervous system.

Preferentially, the compositions of the invention are used in the treatment and/or prevention of atherosclerosis or complications relating to an atheroma. The complications relating to an atheroma typically comprise ischemia, for example myocardial ischemia, coronary diseases, angina pectoris, acute coronary syndrome, myocardial infarction, mesenteric infarction, stroke, aneurysm, or arteriopathy of the lower limbs and consequences thereof (consequences related to hypoxia/ischemia, for example diabetes subsequent to atherosclerosis).

In another preferred mode, the compositions of the invention that are used in the treatment and/or prevention of diseases of the central nervous system are chosen from Alzheimer's disease, Parkinson's disease and lysosomal diseases affecting the central nervous system. The lysosomal diseases affecting the central nervous system are preferentially chosen from Niemann-Pick disease, preferentially Niemann-Pick disease type A, Niemann-Pick disease type B, or Niemann-Pick disease type C.

The methyl cyclodextrin used in the pharmaceutical compositions of the invention preferentially have a degree of molar substitution of between 0.2 and 1.2, and even more preferentially between 0.4 and 0.9. Advantageously, the degree of molar substitution is between 0.6 and 0.8. In one particular embodiment, the methyl cyclodextrin is a methyl-β-cyclodextrin. In another particular embodiment, the methyl cyclodextrin is substituted on the hydroxyl borne by the $C_2$ carbon of the glucopyranose units, or by the $C_3$ and/or $C_6$ carbons of the glucopyranose units or by a combination of the $C_2$, $C_3$ and/or $C_6$, preferably $C_2$ and $C_6$, carbons of the glucopyranose units.

Preferably, the compositions of methyl cyclodextrins comprise one or more methyl-β-cyclodextrins chosen from the group consisting of methyl-β-cyclodextrins substituted on the hydroxyl borne by the $C_2$ carbon of the glucopyranose units, methyl-β-cyclodextrins substituted on the hydroxyl borne by the $C_3$ and/or $C_6$ carbons of the glucopyranose units, and methyl-β-cyclodextrins substituted on the hydroxyl borne by the $C_2$, $C_3$ and/or $C_6$, preferably $C_2$ and $C_6$, carbons of the glucopyranose units, said methyl-β-cyclodextrins having a degree of molar substitution of between 0.6 and 0.8.

Advantageously, the compositions of methyl cyclodextrins comprise at least 50%, 60% or 75% of methyls substituted on the hydroxyl borne by the $C_2$ carbon of the glucopyranose units.

Optionally, the compositions comprising at least one methyl cyclodextrin also comprise a cyclodextrin, in particular β-cyclodextrin, which is unsubstituted, and/or a cyclodextrin, in particular β-cyclodextrin, which is substituted with sulfobutyl ether (SBE-) and hydroxypropyl (HP-) groups, preferably with a degree of molar substitution of between 0.05 and 1.5.

The pharmaceutical compositions used in the context of the present invention can also comprise at least one additional active agent.

The additional active agent is preferentially an active agent used in the treatment of atherosclerosis or complications relating to an atheroma, preferentially
  a statin,
  a platelet aggregation inhibitor or anticoagulant, preferably selected from aspirin, clopidogrel, the new oral anticoagulants such as dabigatran, apixaban or rivaroxaban, and antivitamins K,
  an antihypertensive, preferably selected from angiotensin-converting enzyme inhibitors, such as perindopril, captopril, enalapril, lisinopril or ramipril, and angiotensin II receptor antagonists, such as losartan, valsartan or candesartan, and/or from beta-blockers, such as acebutolol, labetalol, nadolol, oxprenolol, penbutolol, pindolol or propranolol,
  or a combination thereof.

Preferably, the additional active agent is an angiotensin II receptor antagonist, such as losartan, valsartan or candesartan.

The pharmaceutical compositions according to the invention are capable of being administered orally, parenterally, cutaneously or mucosally.

In one particular embodiment, the compositions of the invention are also used for promoting a reduction in circulating fatty acid and triglyceride levels.

In another particular embodiment, the compositions of the invention are used for reducing or preventing atheromatous plaques.

Further, in another particular embodiment, the compositions used in the invention are free or substantially free of phospholipid vesicles.

An additional subject of the invention relates to the non-therapeutic use of a composition comprising at least one methyl cyclodextrin having a degree of molar substitution of between 0.05 and 1.50, preferably of between 0.60 and 0.80, for reducing the triglyceride level and/or for reducing the concentration of free fatty acids and/or for increasing the HDL cholesterol level.

DETAILED DESCRIPTION OF THE INVENTION

The inventors have identified a novel use of a pharmaceutical composition comprising at least one methyl cyclodextrin having a degree of molar substitution of between 0.05 and 1.5, in the treatment and/or prevention of diseases that can be treated and/or prevented by an increase in the HDL cholesterol level and/or by a reduction or prevention of atheromatous plaques.

In particular, the inventors have discovered, surprisingly, that the composition of the invention has the effect of increasing the HDL cholesterol level in an individual, and, in addition, of reducing the circulating fatty acid and triglyceride levels and reducing atheromatous plaques. The inventors have thus demonstrated that the composition of the invention, by virtue of its various properties, can in particular be used in the treatment and/or prevention of diseases associated with overload, and/or with storage and/or with accumulation of cholesterol in the tissues, and also the consequences thereof. In particular, these diseases comprise atherosclerosis or complications relating to an atheroma, and diseases of the central nervous system, in particular Alzheimer's disease, Parkinson's disease or Niemann Pick disease type C.

The invention therefore relates to a pharmaceutical composition comprising at least one methyl cyclodextrin having a degree of molar substitution of between 0.05 and 1.5, for use thereof in the treatment and/or prevention of diseases that can be treated and/or prevented by an increase in the HDL cholesterol level, in particular atherosclerosis or complications relating to an atheroma, and/or diseases of the central nervous system, in particular Alzheimer's disease, Parkinson's disease or Niemann Pick disease type C. It also relates to a pharmaceutical composition comprising at least one methyl cyclodextrin having a degree of molar substitution of between 0.05 and 1.5, for use thereof in the treatment and/or prevention of diseases that can be treated and/or prevented by the reduction of atheromatous plaques or by the prevention of atheromatous plaque formation.

The invention also relates to a pharmaceutical composition comprising at least one methyl cyclodextrin having a degree of molar substitution of between 0.05 and 1.5, for use thereof in the treatment and/or prevention of atherosclerosis or complications relating to an atheroma, and/or diseases of the central nervous system, in particular Alzheimer's disease, Parkinson's disease or Niemann Pick disease type C.

The invention also relates to methods or processes using a pharmaceutical composition comprising at least one methyl cyclodextrin as defined in the present invention, for administration thereof in a therapeutically effective amount in an individual suffering from a disease that can be treated and/or prevented by an increase in the HDL cholesterol level and/or by a reduction or prevention of atheromatous plaques, in particular atherosclerosis or complications relating to an atheroma, and/or diseases of the central nervous system, in particular Alzheimer's disease, Parkinson's disease or Niemann Pick disease type C.

The invention also relates to the use of a pharmaceutical composition comprising at least one methyl cyclodextrin as defined in the present application, for preparing a medicament for treating and/or preventing diseases that can be treated and/or prevented by an increase in the HDL cholesterol level and/or by a reduction or prevention of atheromatous plaques, preferably atherosclerosis or complications relating to an atheroma, and/or diseases of the central nervous system, in particular Alzheimer's disease, Parkinson's disease or Niemann Pick disease type C.

Methyl Cyclodextrins

Cyclodextrins are cyclic oligosaccharides which come from the enzymatic degradation of starch. The three most common natural cyclodextrins are made up of 6, 7 or 8 α-D-glucopyranose units in chair configuration, linked to one another by α-1,4 bonds. They are more commonly referred to as α, β, or γcyclodextrin, respectively. Their three-dimensional structure appears in the form of a truncated cone on the outside of which are the hydroxyl groups representing the highly hydrophilic part of cyclodextrins. The interior of the cone or the cavity of cyclodextrins is made up of the hydrogen atoms borne by the $C_3$ and $C_5$ carbons and also of the oxygen atoms which participate in the glycosidic bond, thus conferring on them a nonpolar nature. Cyclodextrins having a hydrophilic external part and a hydrophobic cavity are generally used for their ability to encapsulate hydrophobic compounds and, therefore, for their hydrophobic active substance-protecting and-solubilizing role. They are thus conventionally found in the fields of food-processing, but also in galenics, where they are used as an excipient in orally administered pharmaceutical formulations or in topically administered cosmetic formulations.

With a view to improving the aqueous solubility of natural cyclodextrins, many derivatives have been synthesized by grafting various groups onto the hydroxyl functions. The glucopyranose units of cyclodextrins in fact each comprise 3 reactive hydroxyl groups, which are borne by the $C_2$, $C_3$ and $C_6$ carbons.

As examples of derivatives, mention may be made of hydroxypropyl cyclodextrins, methyl cyclodextrins and "sulfated" derivatives of cyclodextrin. Frömming and Szetli have in particular shown, in the case of methyl cyclodextrins, that increasing the degree of methylation promotes solubilization up to a degree of molar substitution equal to 2, and that above this, the solubilization decreases.

Some authors have also shown an interest in cyclodextrins and derivatives thereof other than through their pharmaceutical excipient role.

For example, patent application WO 02/43742 describes the role of cyclodextrins or of hydroxypropyl cyclodextrins in cholesterol metabolism, and in particular for promoting cholesterol efflux from macrophages. In this application, the authors recall that cyclodextrins have two mechanisms of action. Cyclodextrins having a high affinity for cholesterol act directly by complexing the membrane cholesterol of macrophages. On the other hand, cyclodextrins having a low affinity for cholesterol act as a catalyst for cholesterol efflux from the cell membrane to an extracellular acceptor which is a phospholipid vesicle. In the latter case, the cholesterol efflux can therefore only take place in the presence of another element which is an exogenous acceptor phospholipid vesicle. Thus, while pharmacological effects on cholesterol are mentioned in the prior art, the therapeutic interest of cyclodextrins remains highly contestable.

This is because high-affinity cyclodextrins, by virtue of their activity in the complexation of cholesterol, would have needed to be administered in considerable amounts, which would not have been pharmaceutically acceptable and which would have caused toxicity problems owing to the large amount of cholesterol solubilized.

As for the low-affinity cyclodextrins, the need to co-administer them with phospholipid vesicles makes this a technology that is much too complex in the light of current knowledge, in particular because phospholipid vesicles are very unstable.

The use of methyl cyclodextrins among other active agents has been suggested in the treatment of atherosclerosis (WO 2006/032905). In particular, this patent application suggests that methyl cyclodextrins are capable of inhibiting the bonds between oxidized LDLs and monocytes. The use of methyl-β-cyclodextrins has been suggested in methods for modulating the inflammatory response by modifying plasma cholesterol levels (US 2008/0032925). The methyl-β-cyclodextrin used in this application is a methyl-3-cyclodextrin which is sold by Sigma Aldrich and which has a degree of molar substitution much higher than 1.5.

In the present invention, the inventors use compositions of particular cyclodextrins which act as an active ingredient with the aim of significantly increasing the plasma HDL cholesterol level while reducing as much as possible the drawbacks associated with toxicity in a patient. The compositions of the invention make it possible to set aside the problems of toxicity by virtue of their particular characteristic, namely a relatively low degree of substitution, in particular of methylation, and also a low affinity for cholesterol.

Surprisingly, and despite their low affinity for cholesterol, the methyl cyclodextrins, and in particular the methyl-β-cyclodextrins, used in accordance with the present invention do not require the addition of phospholipid vesicles in order to exert their effect.

The results obtained by the inventors suggest a different mode of action for these particular methyl cyclodextrins, which appears to involve neither the complexation of cholesterol, nor the catalysis of transport to phospholipid vesicles.

Entirely originally, these methyl cyclodextrins appear to promote the efflux of cholesterol in the form of HDL cholesterol, and not in a form complexed with cyclodextrins or with phospholipid vesicles.

For this reason, the compositions according to the present invention are free or substantially free of phospholipid vesicles. The term "substantially free" signifies herein that the compositions comprise less than 10% of phospholipids by weight relative to the composition, preferably less than 5% by weight and particularly preferably less than 2%, 1% or 0.5% by weight. The term "substantially free" can also be defined by a molar concentration ratio between the amount of cyclodextrin and the amount of phospholipids which is greater than 100, 1000 or 10 000.

The present invention therefore relates to a novel use of a pharmaceutical composition comprising at least one methyl cyclodextrin having a degree of molar substitution of between 0.05 and 1.5 in the treatment and/or prevention of diseases that can be treated and/or prevented by an increase in the HDL cholesterol level and/or by a reduction or prevention of atheromatous plaques.

The invention also relates to a novel use of a pharmaceutical composition comprising at least one methyl cyclodextrin having a degree of molar substitution of between 0.05 and 1.5 in the treatment and/or prevention of atherosclerosis or complications relating to an atheroma, or diseases of the central nervous system, in particular Alzheimer's disease, Parkinson's disease or Niemann Pick disease type C. The term "degree of molar substitution (MS)" is intended to mean the number of hydroxyls substituted, in particular with a methyl group, per glucopyranose unit. It should be noted that the degree of molar substitution (MS) is different than the degree of molecular substitution (DS), which corresponds to the number of hydroxyls substituted, in particular with a methyl group, per cyclodextrin molecule and which therefore takes into account the number of glucopyranose units constituting the methyl cyclodextrin.

The MS can be determined in the present invention by proton nuclear magnetic resonance (NMR), or by mass spectrometry (electrospray ionization mass spectrometry (ESI-MS) or matrix-assisted laser desorption/ionization mass spectrometry (MALDI-MS)). Although these techniques are well known to those skilled in the art, optimal conditions for determining the MS of the methyl cyclodextrins according to the invention are in particular well described in the reference thesis by Romain JACQUET, "Cyclodextrines hydrophiles: caractérisation et etude de leurs propriétés enantioselective et complexante. Utilisation de la chromatographie en phase liquid et de la spectrométrie de masse" ["Hydrophilic cyclodextrins: characterization and study of their enantioselective and complexing properties. Use of liquid chromatography and mass spectrometry"]. Thesis on chemistry and physicochemistry of compounds of biological interest. University of Orleans, 2006. In particular available on: tel.archives-ouvertes.fr (consulted on Nov. 27, 2013), in particular Chapter 2, Part B (pages 59 to 83).

Preferably, the MS is determined by NMR, according to the following method: the measurements are carried out at 25° C. on an Advance DPX 250 MHz apparatus (Bruker, Rheinstetten, Germany). The calibration is performed with the $D_2O$ signal. The samples of methyl cyclodextrin in accordance with the invention, and of native cyclodextrin, i.e. non-methylated cyclodextrin, are prepared at a concentration of 5 mg in 0.75 ml of D20. The solutions are evaporated to dryness under a nitrogen stream and then reconstituted in 0.75 ml of D20. This operation is repeated twice in order to ensure total exchange of the protons of the hydroxyl functions. The MS is calculated from the difference in integration between the spectrum of the native cyclodextrin and that of the methyl cyclodextrin in accordance with the invention. A typical spectrum is shown in FIG. 1.

It should be noted that, although the methyl cyclodextrin used in accordance with the invention can correspond to a pure product, it generally corresponds to a mixture of methyl cyclodextrins of different structures. This is the case, for example, with the products sold by the applicant under the name KLEPTOSE® CRYSMEB, which has in particular the physicochemical properties as determined in the abovementioned thesis by Romain JACQUET, in particular chapter 2, part B (pages 59 to 83).

It results therefrom that the MS measured is, in this case, an average of the substitutions which take place on all of the glucopyranose units of the entire mixture of methyl cyclodextrins.

This mixture can in particular contain residual native cyclodextrin, i.e. non-methylated cyclodextrin, but said cyclodextrin is generally in negligible amounts, in particular less than 1% by dry weight relative to the total dry weight of the methyl cyclodextrin, preferentially less than 0.5%, more preferentially less than 0.1%.

In the context of the invention, the compositions comprise at least one methyl cyclodextrin having a degree of molar substitution of between 0.05 and 1.5. Advantageously, the methyl cyclodextrin has an MS of between 0.1 and 1.4, preferentially between 0.1 and 1.3, preferentially between 0.2 and 1.2, preferentially between 0.3 and 1.1, preferentially between 0.3 and 1, preferentially between 0.5 and 0.9, preferentially between 0.6 and 0.8, for example 0.7, in particular 0.67. For example, the methyl cyclodextrin can have an MS of between 0.10 and 1.40, between 0.10 and 1.30, between 0.10 and 1.20, between 0.15 and 1.40, between 0.15 and 1.30, between 0.15 and 1.20, between 0.20 and 1.40, between 0.20 and 1.30, between 0.20 and 1.20, between 0.20 and 1.10, between 0.25 and 1.40, between 0.25 and 1.30, between 0.25 and 1.20, between 0.25 and 1.10, between 0.15 and 0.90, between 0.15 and 0.80, between 0.25 and 1.00, between 0.25 and 0.90, between 0.25 and 0.80, between 0.30 and 1.40, between 0.30 and 1.30, between 0.30 and 1.20, between 0.30 and 1.00, between 0.50 and 0.90, and between 0.60 and 0.80.

Preferentially, at least 50% of the methyl groups of the methyl cyclodextrin used in the context of the present invention are located at the level of the hydroxyl borne by the $C_2$ carbon of the glucopyranose unit, preferentially between 60% and 80%, typically about 75%.

In parallel, the other methyl groups are generally predominantly located at the level of the hydroxyl borne by the $C_3$ and/or $C_6$ carbon of the glucopyranose unit.

Those skilled in the art know how to determine the distribution of the methyl groups on the hydroxyls of the glucopyranose unit of the methyl cyclodextrin, for example by NMR.

Advantageously, the methyl cyclodextrin used in the context of the present invention comprises 7 α-D-glucopyranose units. It is therefore a methyl-β-cyclodextrin.

In one particular embodiment, the methyl cyclodextrin is a methyl-β-cyclodextrin and has an MS of between 0.05 and 1.5, preferentially of between 0.1 and 1.4, preferentially between 0.1 and 1.3, preferentially between 0.2 and 1.2, preferentially between 0.3 and 1.1, preferentially between 0.4 and 1, preferentially between 0.5 and 0.9, preferentially between 0.6 and 0.8, for example 0.7, in particular 0.67. For example, the methyl cyclodextrin can have an MS of between 0.10 and 1.40, between 0.10 and 1.30, between 0.10 and 1.20, between 0.15 and 1.40, between 0.15 and 1.30, between 0.15 and 1.20, between 0.20 and 1.40, between 0.20 and 1.30, between 0.20 and 1.20, between 0.20 and 1.10, between 0.25 and 1.40, between 0.25 and 1.30, between 0.25 and 1.20, between 0.25 and 1,10, between 0.25 and 1.00, between 0.25 and 0.90, between 0.25 and 0.80, between 0.30 and 1.40, between 0.30 and 1.30, between 0.30 and 1.20, between 0.30 and 1.00, between 0.50 and 0.90, and between 0.60 and 0.80.

The methyl cyclodextrin can be substituted on the hydroxyl borne by the $C_2$ carbon of the glucopyranose units, or by the $C_3$ and/or $C_6$ carbons of the glucopyranose units or by a combination of the $C_2$, $C_3$ and/or $C_6$, preferably $C_2$ and $C_6$, carbons of the glucopyranose units.

In another particular embodiment, the methyl cyclodextrin is a methyl cyclodextrin, preferably a methyl-β-cyclodextrin, in which at least 50% of the methyl groups are located at the level of the hydroxyl borne by the $C_2$ carbon of the glucopyranose unit, preferentially between 60% and 80%, typically about 75%, and has an MS of between 0.05 and 1.5, preferentially of between 0.1 and 1.4, preferentially between 0.1 and 1.3, preferentially between 0.2 and 1.2, preferentially between 0.3 and 1.1, preferentially between 0.4 and 1, preferentially between 0.5 and 0.9, preferentially between 0.6 and 0.8, for example 0.7, in particular 0.67. For example, the methyl cyclodextrin can have an MS of between 0.10 and 1.40, between 0.10 and 1.30, between 0.10 and 1.20, between 0.15 and 1.40, between 0.15 and 1.30, between 0.15 and 1.20, between 0.20 and 1.40, between 0.20 and 1.30, between 0.20 and 1.20, between 0.20 and 1.10, between 0.25 and 1.40, between 0.25 and 1.30, between 0.25 and 1.20, between 0.25 and 1.10, between 0.25 and 1.00, between 0.25 and 0.90, between 0.25 and 0.80, between 0.30 and 1.40, between 0.30 and 1.30, between 0.30 and 1.20, between 0.30 and 1.00, between 0.50 and 0.90, and between 0.60 and 0.80.

In one preferred embodiment, the composition of methyl cyclodextrins comprises one or more methyl-β-cyclodextrins chosen from the group consisting of methyl-β-cyclodextrins substituted on the hydroxyl borne by the $C_2$ carbon of the glucopyranose units, methyl-β-cyclodextrins substituted on the hydroxyl borne by the $C_3$ and/or $C_6$ carbon of the glucopyranose units, and methyl-β-cyclodextrins substituted on the hydroxyl borne by the $C_2$, $C_3$ and/or $C_6$, preferably $C_2$ and $C_6$, carbons of the glucopyranose units and having an MS of between 0.05 and 1.5, preferably of between 0.1 and 1.4, preferentially between 0.1 and 1.3, preferentially between 0.2 and 1.2, preferentially between 0.3 and 1.1, preferentially between 0.4 and 1, preferentially between 0.5 and 0.9, preferentially between 0.6 and 0.8, for example 0.7, in particular 0.67. For example, the methyl cyclodextrin can have an MS of between 0.10 and 1.40, between 0.10 and 1.30, between 0.10 and 1.20, between 0.15 and 1.40, between 0.15 and 1.30, between 0.15 and 1.20, between 0.20 and 1.40, between 0.20 and 1.30, between 0.20 and 1.20, between 0.20 and 1.10, between 0.25 and 1.40, between 0.25 and 1.30, between 0.25 and 1.20, between 0.25 and 1.10, between 0.25 and 1.00, between 0.25 and 0.90, between 0.25 and 0.80, between 0.30 and 1.40, between 0.30 and 1.30, between 0.30 and 1.20, between 0.30 and 1.00, between 0.50 and 0.90, and between 0.60 and 0.80. Preferably, the composition of methyl cyclodextrins comprises at least 50%, 60% or 75% of methyls substituted on the hydroxyl borne by the $C_2$ carbon of the glucopyranose units.

As previously mentioned, the methyl cyclodextrin according to the invention may be a mixture. The mass spectrometry analysis of the KLEPTOSE® CRYSMEB product, which is a methyl-β-cyclodextrin, reveals in particular that it is a polydispersed product, comprising seven predominant methyl cyclodextrin groups, which differ from one another by their DS. This DS, which in theory can range from 0 to 21 for a methyl-β-cyclodextrin, ranges from 2 to 8 in the KLEPTOSE® CRYSMEB product.

Advantageously, the compositions of the invention comprise a mixture of methyl cyclodextrins comprising at least 50%, 60%, 70%, 80% or 90% of methyl cyclodextrins having an MS of between 0.2 and 1.2. Preferably, at least 40%, 50%, 60%, 70%, 80% or 90% of methyl cyclodextrins have an MS of between 0.3 and 1.1. Preferably, at least 30%, 40%, 50%, 60%, 70%, 80% or 90% of methyl cyclodextrins have an MS of between 0.5 and 0.9. Even more preferentially, at least 25%, 30%, 40%, 50%, 60%, 70%, 80% or 90% of methyl cyclodextrins have an MS of between 0.6 and 0.8.

The compositions of methyl cyclodextrins can be optionally prepared by adding various methyl cyclodextrins having defined MSs so as to obtain compositions as defined in the present invention, or they can be obtained as a result of the synthesis thereof.

Thus, in another particular embodiment, the composition of methyl cyclodextrins, preferably of methyl-β-cyclodextrins, has the following substitution profile, expressed as molar percentages:
  0 to 5% of methyl-β-cyclodextrins comprising 2 methyl groups (DS of 2);
  5% to 15% of methyl-β-cyclodextrins comprising 3 methyl groups (DS of 3);
  20% to 25% of methyl-β-cyclodextrins comprising 4 methyl groups (DS of 4);
  25% to 40% of methyl-β-cyclodextrins comprising 5 methyl groups (DS of 5);
  15% to 25% of methyl-β-cyclodextrins comprising 6 methyl groups (DS of 6);
  5% to 15% of methyl-β-cyclodextrins comprising 7 methyl groups (DS of 7);
  0% to 5% of methyl-β-cyclodextrins comprising 8 methyl groups (DS of 8);
the total sum being generally about 100%, although the composition can optionally contain traces of methyl cyclodextrins of different DS, and also traces of native cyclodextrin, i.e. non-methylated cyclodextrin.

The substitution profile can be determined by any technique well known to those skilled in the art, for example by ESI-MS or MALDI-TOF-MS. The optimal conditions for determining the substitution profile using these two methods are in particular widely discussed in the abovementioned thesis by Romain JACQUET, in chapter 2, part B, points 11.3 and 11.2 (page 67 to 82) and in Appendix II.

In one preferred embodiment, the composition of methyl cyclodextrins, preferably of methyl-β-cyclodextrins, is such that at least 50% of the methyl groups are located at the level of the hydroxyl borne by the $C_2$ carbon of the glucopyranose units, preferentially between 60% and 80%, typically about 75%, and has the following substitution profile, expressed as molar percentages:
  0% to 5% of methyl-β-cyclodextrins comprising 2 methyl groups (DS of 2);
  5% to 15% of methyl-3-cyclodextrins comprising 3 methyl groups (DS of 3);
  20% to 25% of methyl-β-cyclodextrins comprising 4 methyl groups (DS of 4);
  25% to 40% of methyl-β-cyclodextrins comprising 5 methyl groups (DS of 5);
  15% to 25% of methyl-β-cyclodextrins comprising 6 methyl groups (DS of 6);
  5% to 15% of methyl-β-cyclodextrins comprising 7 methyl groups (DS of 7);
  0% to 5% of methyl-β-cyclodextrins comprising 8 methyl groups (DS of 8);
the total sum being generally about 100%, although the composition can optionally contain traces of methyl cyclodextrins of different DS, and also traces of native cyclodextrin, i.e. non-methylated cyclodextrin.

It is, moreover, entirely possible to envision varying the proportions of or isolating methyl cyclodextrin molecules or groups of molecules, in particular according to their DS.

Thus, in another particular embodiment, the methyl cyclodextrin is a methyl-β-cyclodextrin which has a DS chosen from an integer ranging from 2 to 8, in particular 2, 3, 4, 5, 6, 7 or 8.

In another preferred embodiment, the methyl cyclodextrin is a methyl-β-cyclodextrin in which at least 50% of the methyl groups are located at the level of the hydroxyl borne by the $C_2$ carbon of the glucopyranose units, preferentially between 60% and 80%, typically about 75%, and which has a DS chosen from an integer ranging from 2 to 8, in particular 2, 3, 4, 5, 6, 7 or 8.

In another particular embodiment, the methyl cyclodextrin, in particular the methyl-β-cyclodextrin, has an MS of between 0.1 and 0.3, in particular between 0.2 and 0.3, especially between 0.20 and 0.30. In another particular embodiment, the methyl cyclodextrin, in particular the methyl-β-cyclodextrin, has an MS of between 0.3 and 0.5, especially between 0.30 and 0.50. In another particular embodiment, the methyl cyclodextrin, in particular the methyl-3-cyclodextrin, has an MS of between 0.5 and 0.6, especially between 0.50 and 0.60. In another particular embodiment, the methyl cyclodextrin, in particular the methyl-β-cyclodextrin, has an MS of between 0.6 and 0.7, especially between 0.60 and 0.70. In another particular embodiment, the methyl cyclodextrin, in particular the methyl-β-cyclodextrin, has an MS of between 0.7 and 0.8, especially between 0.70 and 0.80. In another particular embodiment, the methyl cyclodextrin, in particular the methyl-β-cyclodextrin, has an MS of between 0.8 and 0.9, especially between 0.80 and 0.90. In another particular embodiment, the methyl cyclodextrin, in particular the methyl-β-cyclodextrin, has an MS of between 0.9 and 1.1, especially between 0.90 and 1.10. In another particular embodiment, the methyl cyclodextrin, in particular the methyl-β-cyclodextrin, has an MS of between 1.1 and 1.2, especially between 1.10 and 1.20.

Generally, the methyl cyclodextrin used in accordance with the invention has a reducing sugar content of less than 1% by dry weight, preferentially less than 0.5%.

The composition of methyl-β-cyclodextrins according to the invention can be obtained by means of the process described in U.S. Pat. No. 6,602,860 B1. An example of such a composition is sold by the group ROQUETTE FRERES under the trade name KLEPTOSE® CRYSMEB and has a degree of molar substitution of 0.7 or more specifically of 0.67 methyls per glucose unit.

Optionally, the composition according to the present invention may also comprise a cyclodextrin, in particular β-cyclodextrin, which is unsubstituted, and/or a cyclodextrin, in particular β-cyclodextrin, which is substituted with sulfobutyl ether (SBE-), hydroxyethyl, hydroxypropyl (HP-), carboxymethyl, carboxyethyl, acetyl, triacetyl, succinyl, ethyl, propyl, butyl, sulfate groups, preferably sulfobutyl and hydroxypropyl groups, preferably with a degree of molar substitution of between 0.05 and 1.5.

Optionally, the methyl cyclodextrin according to the invention, in particular the methyl-β-cyclodextrin, can be substituted with additional groups, in particular chosen from those listed above. It may therefore, for example, be a sulfated methyl-β-cyclodextrin.

In one distinct embodiment, the present invention considers also the use, for the treatment of the diseases according to the present invention, of other cyclodextrin derivatives, preferably β-cyclodextrin derivatives, having a degree of molar substitution in accordance with the present invention, i.e. of between 0.05 and 1.5, preferentially of between 0.1 and 1.4, preferentially between 0.1 and 1.3, preferentially between 0.2 and 1.2, preferentially between 0.3 and 1.1, preferentially between 0.4 and 1, preferentially between 0.5 and 0.9, preferentially between 0.6 and 0.8, for example 0.7. These cyclodextrin derivatives, preferably β-cyclodextrin derivatives, are substituted with a group chosen from sulfobutyl ethers (SBE-) and hydroxypropyls (HP-). Preferably, these substitutions are mainly borne by the $C_2$ carbon of the glucopyranose units, typically at 50%, 60%, 70% or 80%.

In one alternative mode of the invention, the methyl cyclodextrins as defined in the present application and composed of α-D-glucopyranose units linked to one another by α-1,4 bonds can be partially or totally replaced with α-D-glucopyranose units linked to one another by α-1,6 bonds, in the pharmaceutical compositions of the present invention.

Application

In the context of the present invention, the pharmaceutical compositions comprising at least one methyl cyclodextrin as defined in the present application are used in the treatment and/or prevention of diseases that can be treated and/or prevented by an increase in the HDL cholesterol level and/or by a reduction or prevention of atheromatous plaques, in particular atherosclerosis or complications relating to an atheroma, and/or diseases of the central nervous system, in particular Alzheimer's disease, Parkinson's disease or Niemann Pick disease type C.

In the context of the present invention, the increase in the HDL cholesterol level is measured in any type of biological fluid. It is preferentially the plasma HDL cholesterol level. This HDL cholesterol level can be measured by any method known to those skilled in the art, for example by precipitation, or by direct homogeneous-phase methods using immunological techniques. It is also possible to assay the protein part (Apo A1 protein) making up the HDLs.

The HDL cholesterol level is generally expressed as number of moles of cholesterol transported by the high-density lipoproteins (HDLs) per liter of blood. The HDL cholesterol is considered to be "good cholesterol", unlike the cholesterol transported by the LDLs.

According to the invention, the diseases that can be treated and/or prevented by an increase in the HDL cholesterol level are all the diseases of which the symptoms and/or the causes disappear or are reduced in a patient when the HDL cholesterol level is higher than the HDL cholesterol level before treatment. Preferably, the diseases are those that can be treated and/or prevented by an increase in the HDL cholesterol level. The term "increase" can be understood to mean an increase in the HDL cholesterol level of at least 5%, 7.5%, 10%, 15% or 20%.

The diseases that can be treated and/or prevented by an increase in the HDL cholesterol level are preferentially diseases associated with overload, and/or with storage and/or with accumulation of cholesterol in the tissues, and also the consequences thereof.

As examples of diseases that can be associated with overload, and/or with storage and/or with accumulation of cholesterol in the tissues, mention may be made of cardiovascular diseases, vascular diseases, occlusive peripheral arterial diseases such as atherosclerosis or complications relating to an atheroma.

As other examples, mention may be made of diseases of the central nervous system that can be associated with overload, and/or with storage and/or with accumulation of cholesterol in the tissues of the central nervous system. Such diseases comprise, in a nonlimiting manner, Alzheimer's disease, Parkinson's disease, and lysosomal diseases affecting the central nervous system.

As examples of lysosomal diseases, mention may be made, without limitation, of Niemann-Pick disease, such as Niemann-Pick disease type A, Niemann-Pick disease type B, or Niemann-Pick disease type C.

A particular example is Niemann-Pick disease type C, characterized by an accumulation of non-esterified cholesterol in the central nervous system (CNS).

In one preferred embodiment, the disease is selected from Alzheimer's disease, Parkinson's disease and Niemann-Pick disease type C.

Another particular example concerns Alzheimer's disease. The accumulation of cholesterol in the brain can also be responsible for Alzheimer's disease, and an increase in the HDL cholesterol level promotes transport thereof to the liver where it is degraded. Data suggest with great emphasis that a dysfunction of cholesterol metabolism in the brain and in the vascular system is in all probability closely involved in Alzheimer's disease.

The presence of a cholesterol level that is too high is often considered to be a risk factor for the occurrence of cognitive disorders, of dementia or of Parkinson's disease. The involvement of cholesterol in an increased risk of Parkinson's disease has also been mentioned in several studies.

In this context, a treatment of which the effect is an increase in the HDL cholesterol level which contributes to the transport of excess cholesterol to the liver, where it is degraded, makes complete sense for this application. Indeed, a body of observations, of statistical data and of experiments at the molecular level leads to an increasingly significant role being given to cholesterol metabolism in the generation of Alzheimer's disease. In particular, a convergence between atherosclerosis and Alzheimer's disease (AD) and also between Alzheimer's disease and Niemann-Pick disease type C has been solidly established. The latter rare disease is characterized by the excessive accumulation of cholesterol in nerve cells.

Moreover, the present invention also relates to the diseases that can be treated and/or prevented by a reduction or prevention of atheromatous plaques. The term "reduction of atheromatous plaques" is preferably intended to mean that the plaques have a smaller surface area in the presence of the treatment than in the absence thereof. Notably, the reduction of the surface area of the plaques of 10%, 20%, 30%, 40% or 50%. Preferably, this reduction is at least of 30% or 40%. The surface area of the atheromatous plaques can be determined by any method known to those skilled in the art and in particular medical imaging methods such as MM (magnetic resonance imaging). The term "prevention of atheromatous plaques" is intended to mean a slowing down of the development or the formation of these plaques.

The diseases that can be treated and/or prevented by a reduction or prevention of atheromatous plaques are in particular cardiovascular diseases, vascular diseases, and preferentially occlusive peripheral arterial diseases such as atherosclerosis or complications relating to an atheroma.

According to the invention, the diseases that can be treated and/or prevented are preferentially atherosclerosis or complications relating to an atheroma, Alzheimer's disease, Parkinson's disease or Niemann-Pick disease type C, and advantageously atherosclerosis or complications relating to an atheroma.

The complications relating to an atheroma which are treated and/or prevented by using a pharmaceutical composition comprising at least one methyl cyclodextrin of the invention are, in a nonlimiting manner, ischemia, for example myocardial ischemia, coronary diseases, angina pectoris, acute coronary syndrome, myocardial infarction, mesenteric infarction, stroke, aneurysm or arteriopathy of the lower limbs.

In another particular embodiment, the compositions of the invention that are used also comprise at least one additional active agent. The additional active agent is preferentially chosen from the group of active agents known by those skilled in the art for treating and/or preventing atherosclerosis or complications relating to an atheroma.

The subjects to be treated are preferably human beings or animals, preferably human beings. They may have a proven (diagnosed or established) disease or be at risk of developing this disease. In particular, in the present invention, the term "treatment" is intended to mean a decrease in the causes or symptoms of a disease, delayed appearance of the disease, slowing down of the development thereof, but also curing thereof.

As examples of active agents used in the treatment of atherosclerosis or complications relating to an atheroma, mention may be made of:
- statins;
- antihypertensive agents, in particular:
  - angiotensin-converting enzyme inhibitors, for example perindopril, captopril, enalapril, lisinopril or ramipril;
  - angiotensin II receptor antagonists, also known as "sartans", such as losartan, valsartan or candesartan;
  - beta-blockers, such as acebutolol, labetalol, nadolol, oxprenolol, penbutolol, pindolol or propranolol;
- platelet aggregation inhibitors or anticoagulants, in particular:
  - aspirin;
  - clopidogrel (PLAVIX®);
  - new oral anticoagulants such as dabigatran/Pradaxa®, apixaban/Eliquis®, rivaroxaban/Xarelto®, indicated in the prevention of phlebitis, embolisms or strokes in the atrial fibrillation indication;
  - antivitamins K, which are very effective but are used little today since they require very close monitoring of coagulation.

Preferably, the additional active agent will be preferentially chosen from angiotensin II receptor antagonists.

The compositions according to the present invention are capable of being administered orally, parenterally, mucosally or cutaneously. The parenteral route preferentially comprises subcutaneous, intravenous, intramuscular or intraperitoneal administration, although the latter is rather reserved for animals. The mucosal route preferentially comprises nasal administration, pulmonary administration or administration via the rectal mucosa. The cutaneous route advantageously comprises the dermal route, in particular via a transdermal device, typically a patch. Other routes of administration concerning more particularly diseases affecting the central nervous system (CNS), in particular Niemann-Pick disease type C, Parkinson's disease or Alzheimer's disease, are the intrathecal or spinal route.

The compositions according to the present invention also comprise a pharmaceutically acceptable excipient. Use may be made of any excipient suitable for the galenical forms known to those skilled in the art, in particular in view of a systemic administration, preferentially in view of an oral administration, of a parenteral administration, of a cutaneous or mucosal administration, in particular via the subcutaneous, intravenous, intramuscular, intraperitoneal, nasal, pulmonary, rectal, dermal, intrathecal or spinal route. Mention may be made, for example, of buffered isotonic physiological saline solutions, etc., compatible with pharmaceutical use and known to those skilled in the art. The compositions may contain one or more agents or carriers chosen from dispersants, solubilizing agents, stabilizers, preservatives, etc. Agents or carriers that can be used in (liquid and/or injectable) formulations are in particular methylcellulose, hydroxymethylcellulose, carboxymethylcellulose, polysorbate 80, mannitol, gelatin, lactose, vegetable oils, acacia, liposomes, etc. The compositions can be formulated in the form of injectable suspensions, gels, oils, tablets, suppositories, powders, gel capsules, capsules, aerosols, etc., optionally by means of galenical forms or of devices which provide sustained and/or delayed release. For this type of formulation, an agent such as cellulose, carbonates or starches is advantageously used.

It is advantageously possible to imagine a galenical form in which the cyclodextrin according to the invention is administered in a form complexed with a lipid substance, so as to allow it to pass into the bloodstream after administration by non-invasive routes, and/or in the case where crossing the blood-brain barrier is desired, so as to allow the crossing of this barrier. Among these lipid substances, mention may be particularly made of tocopherol.

The compositions that can be administered to an individual in the context of the invention comprise between 1 and 100 mg/kg, preferentially between 20 and 70 mg/kg, even more preferentially between 30 and 50 mg/kg, and even more preferably 40 mg/kg, of methyl cyclodextrin as defined in the present invention, relative to the total weight of the individual. Of course, those skilled in the art are able to adjust the dose of methyl cyclodextrin defined in the present application according to the weight of the individual to be treated.

Advantageously, the compositions are therefore capable of being administered in a therapeutically effective amount to an individual suffering from a disease that can be treated and/or prevented by an increase in the HDL cholesterol level, or to an individual predisposed to developing such a disease. The twit "therapeutically effective amount" is intended to mean a sufficient amount of composition that could be administered to an individual in order to prevent and/or treat a disease as defined in the present invention.

The compositions used in the invention can be administered according to variable modes. In particular, they can be injected one to five times per week for 1, 2, 3 or 4 weeks, or even 1, 2, 3 or several months. The administration modes also include treatments at intervals several weeks or several months apart. For the treatment and/or prevention of atherosclerosis in particular, an administration at an interval of 3 to 6 months, which can range up to 12 months, having a duration of one week, will advantageously be envisioned.

Another subject of the invention relates to the use of the pharmaceutical compositions as defined in the present application, for also promoting a reduction in circulating fatty acid and triglyceride levels.

An additional subject of the invention relates to the use of the pharmaceutical compositions as defined in the present application, for reducing atheromatous plaques.

The use of the compositions of the invention makes it possible at the same time to increase the HDL cholesterol level, to reduce the levels of triglycerides and fatty acids circulating in the blood and to reduce the atheromatous plaques. The composition of the invention also makes it possible to induce a decrease in MMP-9s responsible for making atheromatous plaques fragile, and therefore complications relating to atheroma. All these effects are obtained without modifying the LDL-cholesterol level, and without any toxicity having been noted. The decrease in MMP-9s suggests, moreover, the advantage of the composition according to the invention for use in the treatment and/or prevention of cancer.

The compositions as defined in the present application are also of interest in healthy subjects. The compositions of the invention make it possible in particular to reduce the triglyceride level and the concentration of free fatty acids and to increase the level of good cholesterol (HDL cholesterol), thus promoting good health of the subject. Consequently, the present invention also relates to a non-therapeutic use of the compositions of methyl cyclodextrins as previously defined in the present application for reducing the triglyceride level and/or for reducing the concentration of free fatty acids and/or for increasing the level of good cholesterol (HDL cholesterol). Thus, the composition of methyl cyclodextrins according to the present invention can be used as a nutraceutical composition, health food, functional food or food supplement. The term "nutraceutical composition, health food, functional food" is intended to mean herein a food which contains ingredients having effects beneficial to health or capable of improving physiological functions. The term "food supplement" is intended to mean a foodstuff of which the purpose is to supplement the normal diet.

The normal or healthy subjects most suited to profiting from these compositions are individuals aged 40 or over, preferably aged 50 or over, and for example aged between 50 and 70. These subjects are not suffering from any pathological condition.

The composition intended for food for human consumption can take any form, and in particular can be a liquid, a paste or a solid. In particular, the composition may be a dairy product such as cheese, butter, yoghurt or cream, a fruit-based product such as a fruit juice, a compote or a fruit jelly, a drink, or a solid food, such as a snack, a cookie, or the like. It can also be formulated in the form of tablets, a powder, a capsule, a tablet, a solution, a concentrate, a syrup, a suspension or a dispersion.

The examples which follow serve to illustrate the invention and show other aspects and advantages of the invention and should be considered to be nonlimiting.

FIGURE LEGENDS

Figure 2:
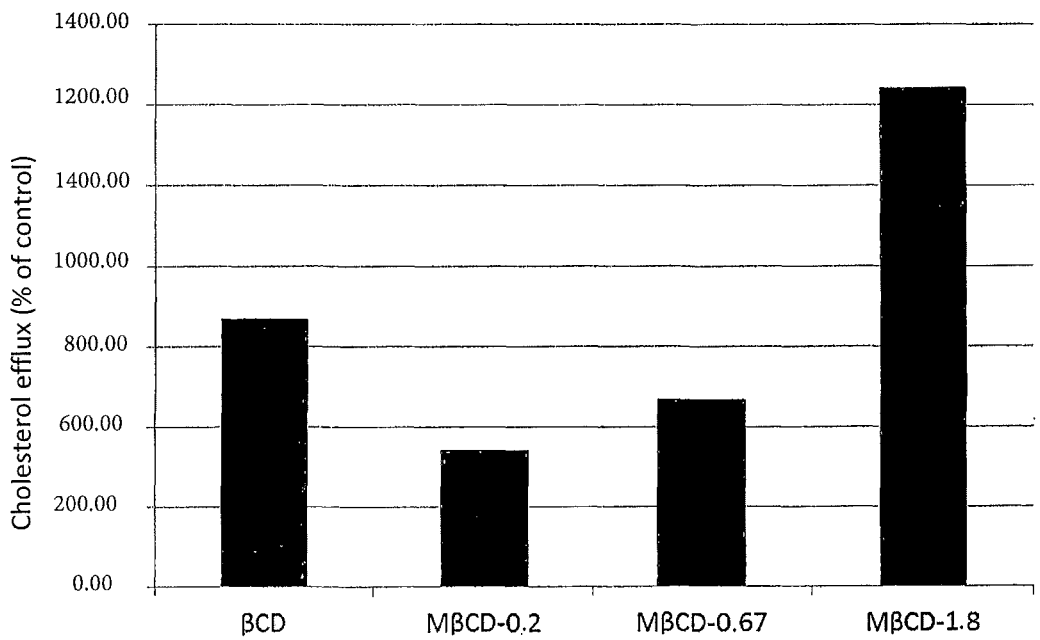
Figure 3:
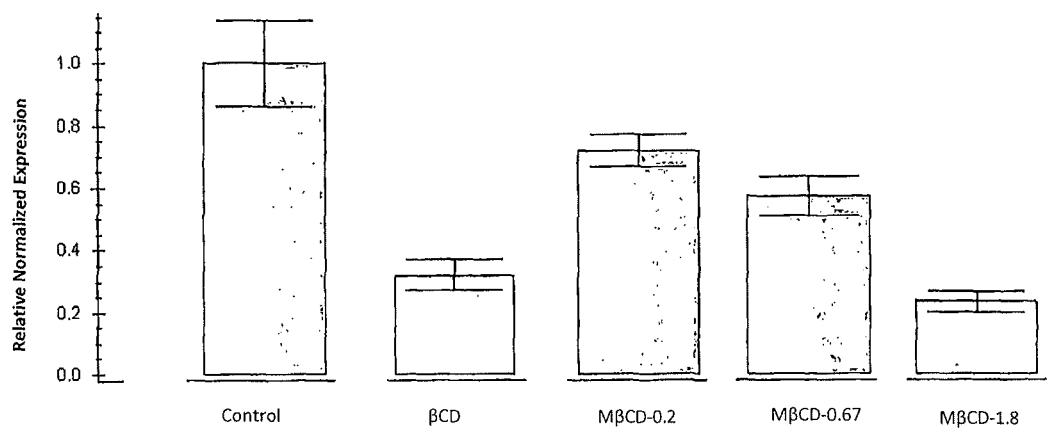
Figure 4:
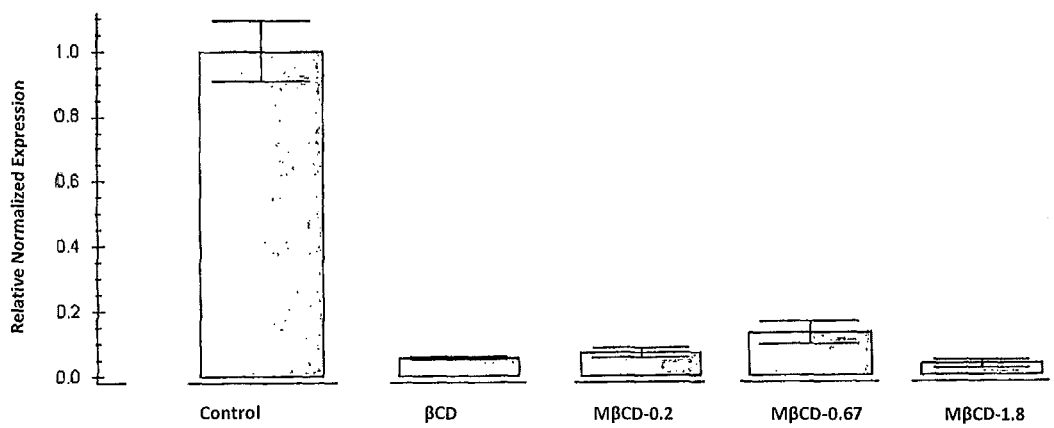
Figure 5:
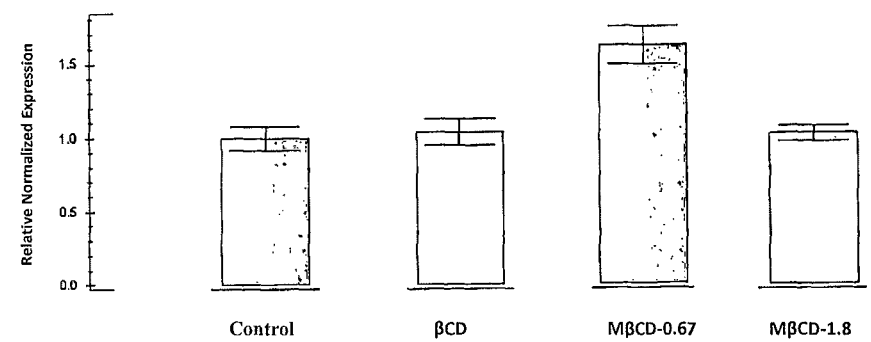

FIG. 1: $^1$H NMR spectrum of a methyl-β-cyclodextrin according to the invention.
FIG. 2: Measurement of cholesterol effluxes as a function of the MS of the methyl-β-cycicodextrins.
FIG. 3: Expression of the ABCA1 transporter as a function of the MS of the methyl-β-cyclodextrins.
FIG. 4: Expression of the ABCG1 transporter as a function of the MS of the methyl-β-cyclodextrins.
FIG. 5: Expression of the SR-B1 receptor as a function of the MS of the methyl-β-cyclodextrins.

EXAMPLES

Example 1: In Vivo Study of the Methyl Cyclodextrins of the Invention

Male 11-week-old Apo E−/− mice were used.
The composition of methyl cyclodextrin used is the commercial product KLEPTOSE® CRYSMEB (ROQUETTE).
The mice were divided up into 6 groups:
2 groups of mice subjected to a normal diet for 16 weeks. This atheroma model is characterized by an early disease. The first group was treated with a placebo solution (control mice, n=9), the second group was treated with 40 mg/kg KLEPTOSE® CRYSMEB (treated mice, n=12);
2 groups of mice subjected to a cholesterol-rich diet for 11 weeks. This atheroma model is characterized by an advanced disease. The first group was treated with a placebo solution (control mice, n=9), the second group was treated with 40 mg/kg KLEPTOSE® CRYSMEB (treated mice, n=11).

The treatments were carried out by intraperitoneal injection of a volume of 200 µl of placebo (PBS solution) or of KLEPTOSE® CRYSMEB solution, three times per week. Blood samples were taken when the animals were sacrificed, after the 16 or 11 weeks of treatment, by cardiac puncture, in order to determine the impact of the treatment on the lipidemia.

Other values, such as glycemia, hematocrit values (hemoglobin level, erythrocyte, leukocyte, lymphocyte and platelet counts) were measured without any difference being observed between the various groups of mice. Consequently, these results are not presented herein.

After sacrifice, quantification of the atheromatous surface area was moreover carried out on each group of mice by computer-assisted morphometry, on 4 aortic sections of 10 µm stained with hematoxilin and Oil-red-O, taken at 200, 400, 600 and 800 µm after the start of the cuspid valve, according to the method described in the article "Caligiuri G, Groyer E, Khallou-Laschet J, Al Haj Zen A, Sainz J, Urbain D et al. Reduced immunoregulatory CD31+ T cells in the blood of atherosclerotic mice with plaque thrombosis. Arterioscler Thromb Vasc Biol 2005; 25:1659-1664." Immunohistochemical labelings of atheromatous plaque MMP-9s were also carried out and quantified in order to determine the fragility of said plaques (R&D Systems kit).

The results obtained are presented in tables 1 and 2.

TABLE 1

Mice subjected to a normal diet and treated with a composition of methyl cyclodextrins according to the invention

| | Control mice (n = 9) | Treated mice (n = 12) | p |
|---|---|---|---|
| Body weight (g) | 31.84 ± 2.70 | 30.71 ± 3.09 | 0.4137 |
| Lipidemia | | | |
| Total cholesterol (mmol/l) | 14.49 ± 1.65 | 14.19 ± 3.02 | 0.8070 |
| LDL cholesterol (mmol/l) | 9.29 ± 1.22 | 9.76 ± 2.34 | 0.8621 |
| HDL cholesterol (mmol/l) | 2.77 ± 0.15 | 3.03 ± 0.38 | 0.1451 |
| Triglycerides (mmol/l) | 2.20 ± 0.66 | 1.65 ± 0.55 | 0.0491 |
| Free fatty acids (mmol/l) | 1.33 ± 0.36 | 1.03 ± 0.40 | 0.0955 |
| Aortic valve sinus | | | |
| Oil-red-O, ×10$^3$ µm$^2$ | 295.06 ± 36.25 | 246.14 ± 46.38 | 0.0278 |
| MMP-9, % | 6.35 ± 4.78 | 3.26 ± 4.84 | 0.0481 |
| Aorta | | | |
| Plaque surface area (%) | 5.56 ± 2.65 | 3.39 ± 1.26 | 0.0278 |

The values are expressed as mean ± standard deviation.
The p values are calculated according to the Mann-Whitney U test.

TABLE 2

Mice subjected to a cholesterol-rich diet and treated with a composition of methyl cyclodextrins according to the invention

|  | Control mice (n = 9) | Treated mice (n = 11) | p |
|---|---|---|---|
| Body weight (g) | 30.44 ± 2.34 | 28.34 ± 2.80 | 0.1194 |
| *Lipidemia* | | | |
| Total cholesterol (mmol/l) | 21.48 ± 1.37 | 20.17 ± 1.37 | 0.4119 |
| LDL cholesterol (mmol/l) | 17.05 ± 3.81 | 17.51 + 4.00 | 0.9999 |
| HDL cholesterol (mmol/l) | 3.44 ± 0.49 | 4.16 ± 0.82 | 0.0334 |
| Triglycerides (mmol/l) | 1.47 ± 0.65 | 0.90 ± 0.36 | 0.0136 |
| Free fatty acids (mmol/l) | 0.99 ± 0.25 | 0.75 ± 0.20 | 0.0310 |
| *Aortic valve sinus* | | | |
| Oil-red-O, ×10$^3$ μm$^2$ | 465.56 ± 66.99 | 439.45 ± 86.58 | 0.1119 |
| MMP-9, % | 22.80 ± 15.88 | 12.45 ± 9.80 | 0.4119 |
| *Aorta* | | | |
| Plaque surface area (%) | 24.73 ± 6.75 | 15.00 ± 7.56 | 0.0200 |

The values are expressed as mean ± standard deviation.
The p values are calculated according to the Mann-Whitney U test.

It should be noted in these results that the shift in the values resulting from the treatment are obtained not only after a rich diet, but also surprisingly and favorably following a normal diet, not enriched with cholesterol.

In both cases in fact, an increase in the HDL cholesterol level was observed, showing the advantage of the methyl cyclodextrins according to the invention for use in the treatment and/or prevention of diseases that can be treated and/or prevented by an increase in the HDL cholesterol level.

In both cases, the atheromatous plaque surface area is significantly reduced. A substantial reduction, of close to 40%, in the atheromatous surface area was observed. These results demonstrate the advantage of the methyl cyclodextrins according to the invention, for use in the treatment and/or prevention of atherosclerosis or complications relating to an atheroma.

A reduction in the level of triglycerides, free fatty acids and in the level of MMP-9 was observed, and reinforces the advantage of the methyl cyclodextrins according to the invention, for use in the treatment and/or prevention of atherosclerosis or complications relating to an atheroma.

Example 2: In Vitro Study of the Methyl Cyclodextrins of the Invention

This example illustrates the effects of various cyclodextrins on cholesterol effluxes tested with aortic endothelial cells. The aortic endothelium is the atheromatous plaque tissue which is in direct contact with the blood compartment, and therefore in direct contact with the HDLs.

Material

Cells: The endothelial cells were adult bovine aortic endothelial cells (ABAEs).

Cyclodextrins: the cyclodextrins used were the following: a non-methylated β-cyclodextrin, hereinafter denoted "β-CD", a methyl-β-cyclodextrin having an MS of 0.2, hereinafter denoted "MβCD-0.2", a methyl-β-cyclodextrin having an MS of 0.67 (KLEPTOSE® CRYSMEB, ROQUETTE FRERES), hereinafter denoted "MβCD-0.67", a methyl-β-cyclodextrin having an MS of 1.8 (RAMEB®, CYCLOLAB), hereinafter denoted "MβCD-1.8".

Incubation of the Cells with the Cyclodextrins:

0.5 μCi/ml of 3H-cholesterol was incorporated into serum (10% horse serum/calf serum (HS/CS)) for 6 hours at 37° C. for the purpose of obtaining a culture medium enriched with radioactive cholesterol. After this incorporation, the culture medium was finalized by incorporation of DMEM (Dulbecco's Modified Eagle's medium) supplemented with 10% HS, 10% CS, 1 ng/ml bFGF (basic fibroblast growth factor), 2 mM glutamine and 50 μg/ml gentamicin.

The cells were then cultured in this radioactive medium for 36 hours in order to allow them to incorporate the radioactive cholesterol. The medium was then removed and the cells were rinsed twice with warm DMEM containing 0.1% of bovine serum albumin (BSA). The cells were then cultured in DMEM/1 ng/ml bFGF containing 1 mM of each cyclodextrin for 24 hours (1.4 ml/well).

A. Measurement of the Cholesterol Captured by the Cyclodextrins

In this example, the applicant studied the effect of the cyclodextrins on the cholesterol effluxes, according to their degree of methylation.

Two hours after the beginning of the incubation in the presence of each cyclodextrin, 500 of medium were removed and the radioactive cholesterol captured by the cyclodextrin was assayed by means of a scintillation counter (Tri-carb 2100TR). The radioactivity was measured in disintegrations per minute (DPM). The capacity of each cyclodextrin to capture cellular cholesterol was then estimated by performing the following calculation: ((1.4 ml/0.5 ml)× DPM measured).

The values were then converted into the form of percentages which are compared with the condition incubated without cyclodextrin (control) representing 100%.

Each experiment was carried out in triplicate and repeated twice.

The results obtained are presented in FIG. 2.

Results:

The MβCD-0.2 and MβCD-0.67 in accordance with the invention cause a much lower cholesterol efflux than the βCD and MβCD-1.8 not in accordance with the invention. The inventors therefore demonstrated a lower affinity with respect to cholesterol for the methylated cyclodextrins according to the invention illustrating an efflux of cholesterol in the form of HDL cholesterol and not in a form of cholesterol complexed with cyclodextrins, or with phospholipid vesicles.

B. Expression of the Transporters Responsible for Intracellular Cholesterol Efflux: ABCA1 and ABCG1

In this example, the applicant studied the expression of two transporters responsible for cholesterol effluxes, the ABCA1 receptor and the ABCG1 receptor, following treatment with cyclodextrins having various degrees of methylation.

After 24 hours of treatment with each cyclodextrin, the cells were rinsed twice in cold PBS (8 g/l NaCl, 0.2 g/l KCl, 0.2 g/l KH$_2$PO$_4$, 2.87 g/l NA$_2$HPO$_4$ (12H$_2$O), pH 7.4) and lyzed using 500 μl of RLT lysis buffer (Biorad). Three wells were used and pooled for each condition. The messenger RNA (mRNA) purification was carried out using the RNeasy total RNA extraction kit (Qiagen) according to the manufacturer's recommendations. At the end of this purification step, the mRNA concentration was estimated by virtue of the absorbance values obtained at 260, 280 and 320 nm. The purity of the samples was verified by calculating the 260/280 ratio and only the samples having a value greater than 2 were considered for our studies.

For each sample, the cDNAs were synthesized from 250 ng of mRNA using the iScript Reverse Transcription Supermix kit (Biorad) according to the manufacturer's instructions. The real-time PCR experiments were carried out using the Sso Fast EvaGreen Master Mix kit (BioRad) and the primers designed and optimized by the applicant (table 3).

TABLE 3

| mRNA | Species | Sequences | | Accession No |
|---|---|---|---|---|
| ABCA1 | Bos taurus | F 5'-gtgtctcgcctgttctcag-3' | (SEQ ID No 1) | NM_001024693 |
| | | R 5'-gaaacatcacctcctgccg-3' | (SEQ ID No 2) | |
| ABCG1 | Homo sapiens | F 5'-gaggaagaaaggatacaagacc-3' | (SEQ ID No 3) | BC029158 |
| | | R 5'-gtcagtatctccttgaccattt-3' | (SEQ ID No 4) | |

The amplification was carried out over the course of 40 cycles with a hybridization temperature of 60° C. using the Biorad CFX96 thermocycler. For each pair of primers, the amplification specificity was verified by producing melting curves and the efficiency was determined by producing dilution curves. The expression levels measured were then normalized on the expression levels of β-actin and cyclophillin B using the ΔΔCt method. Each experiment was carried out in triplicate and repeated twice.

The results obtained are presented in FIGS. 3 and 4.

Results:

The results show that, in response to a treatment with a cyclodextrin, generally, the expression of the ABCA1 and ABCG1 receptors by the endothelial cells decreases compared with the control.

In particular, the MβCD-0.2 and MβCD-0.67 according to the invention cause a lower decrease in the ABCA1 et ABCG1 receptor expression, compared with the βCD and MβCD-1.8.

By combining these results with those obtained above (point A), the inventors showed that the βCD and MβCD-1.8 not in accordance with the invention induced a rapid and considerable efflux of cholesterol and a more intense reaction of the cell by strongly decreasing ABCA1 and ABCG1 receptor expression.

On the other hand, the MβCD-0.2 and MβCD-0.67 in accordance with the invention, even though they induce lower cholesterol effluxes, decrease ABCA1 and ABCG1 receptor expression to a much lesser extent.

The cholesterol efflux kinetics of the methylated cyclodextrins in accordance with the invention are thus completely different than those of the cyclodextrins not in accordance with the invention. It is postulated by the inventors that these particular kinetics of the methylated cyclodextrins in accordance with the invention have the advantage of causing less disruption to cellular cholesterol homeostasis.

C. Study of the Expression of the SR-B1 Receptor (Scavenger Receptor Class B Member 1), an HDL Receptor, of Endothelial Cells Treated with Cyclodextrins In this example, the applicant studied the effect of the cyclodextrins on the expression of an HDL receptor, the SR-B1 receptor, according to their degree of methylation.

One of the roles of SR-B1 receptors in the endothelium is to promote the efflux of free cholesterol to the HDLs in the circulation.

The expression of the SR-B1 receptor was studied according to the protocol as previously described, using primers designed and optimized by the applicant (table 4).

TABLE 4

| mRNA | Species | Sequences | | Accession No |
|---|---|---|---|---|
| SCARB1 | Bos taurus | F 5'-cccttaatccacctcatcaatc-3' | (SEQ ID No 5) | NM_174597 |
| | | R 5'-gaagtttttgacccctgtgaac-3' | (SEQ ID No 6) | |

Each experiment was carried out in triplicate and repeated twice.

The results obtained are presented in FIG. 5.

Results:

The MβCD-0.67 according to the invention causes a strong increase in the expression of the SR-B1 receptor, of approximately 50% of the basal expression.

In conclusion, the inventors showed that the methyl cyclodextrins according to the present invention exhibited a low affinity for cholesterol, limited the decrease in transporters responsible for cholesterol efflux and increased the expression of the HDL receptor SR-B1, this having the effect of promoting the transport of cytoplasmic cholesterol to the blood and therefore of increasingly plasma cholesterol level, in particular the HDL cholesterol. The inventors therefore demonstrated that methyl cyclodextrins according to the invention, despite their low affinity for cholesterol, did not require the addition of phospholipid vesicles in order to exert their effects illustrated by the in vivo results of example 1 (tables 1 and 2).

These results reinforce the advantage of the methyl cyclodextrins according to the invention, for use in the treatment and/or prevention of diseases that can be treated and/or prevented by an increase in the HDL cholesterol level.

The invention claimed is:

1. A method of treating diseases of the central nervous system, comprising increasing the HDL without modifying the LDL-cholesterol level of a subject by administrating a pharmaceutical composition comprising at least one methyl-β-cyclodextrin having a degree of molar substitution between 0.2 and 1.5, to a subject having diseases of the central nervous system, wherein the diseases of the central nervous system are selected from the group consisting of Alzheimer's disease, Parkinson's disease, and lysosomal diseases affecting the central nervous system.

2. The method of claim 1, wherein the methyl-β-cyclodextrin has a degree of molar substitution between 0.2 and 1.2.

3. The method of claim 2, wherein the methyl-β-cyclodextrin has a degree of molar substitution between 0.6 and 0.8.

4. The method of claim 3, wherein the methyl-β-cyclodextrins comprises one or more methyl-β-cyclodextrins selected from the group consisting of methyl-β-cyclodextrins substituted on the hydroxyl borne by the $C_2$ carbon of the glucopyranose units, methyl-β-cyclodextrins substituted on the hydroxyl borne by the $C_3$ and/or $C_6$ carbons of the glucopyranose units, and methyl-β-cyclodextrins substituted on the hydroxyl borne by the $C_2$, $C_3$ and/or $C_6$ carbons of the glucopyranose units.

5. The method of claim 1, wherein the methyl-β- cyclodextrin is substituted on the hydroxyl borne by the $C_2$ carbon of the glucopyranose units, or by the $C_3$ and/or $C_6$ carbons of the glucopyranose units, or by a combination of the $C_2$, $C_3$ and/or $C_6$ carbons of the glucopyranose units.

6. The method of claim 1, wherein the lysosomal diseases affecting the central nervous are selected from Niemann-Pick disease, Niemann-Pick disease type A, Niemann-Pick disease type B, or Niemann-Pick disease type C.

7. The method of claim 1, wherein the composition of methyl-β-cyclodextrins comprises at least 50% of methyls substituted on the hydroxyl borne by the $C_2$ carbon of the glucopyranose units.

8. The method of claim 1, wherein the composition comprising at least one methyl-β-cyclodextrin also comprises at least one of cyclodextrin which is unsubstituted and cyclodextrin substituted with sulfobutyl ether (SBE) or hydroxypropyl (HP) groups.

9. The method of claim 1, wherein said composition is free of phospholipid vesicles.

10. The method of claim 1, wherein said methyl-β-cyclodextrin is the sole active ingredient of said pharmaceutical composition.

11. A method of treating diseases of the central nervous system, comprising administrating a pharmaceutical composition comprising at least one methyl-β-cyclodextrin having a degree of molar substitution between 0.2 and 1.5 to a subject having diseases of the central nervous, increasing the level of HDL without modifying the LDL-cholesterol level in the subject and thereby reducing at least one of overload, storage and accumulation of cholesterol in the tissues of the central nervous system, wherein the diseases of the central nervous system are selected from the group consisting of Alzheimer's disease, Parkinson's disease, and lysosomal diseases affecting the central nervous system.

12. The method of claim 11, wherein said pharmaceutical composition further comprises at least one additional active agent.

13. The method of claim 12, wherein the active ingredient is tocopherol.

14. The method of claim 11, wherein diseases are selected Alzheimer's disease, Parkinson's disease or Niemann Pick disease type C.

15. The method of claim 11, wherein said pharmaceutical composition is administered without the addition of phospholipid.

16. The method of claim 11, wherein said methyl-β-cyclodextrin is the sole active ingredient of said pharmaceutical composition.

17. A method of treating diseases of the central nervous system, comprising administering a pharmaceutical composition comprising at least one methyl-β-cyclodextrin having a degree of molar substitution between 0.2 and 1.5 to a subject having diseases of the central nervous, and increasing expression of the HDL receptor SR-B1, thereby promoting transport of cytoplasmic cholesterol to blood of the subject and increasing plasma HDL cholesterol without modifying the LDL-cholesterol level, wherein the diseases of the central nervous system are selected from the group consisting of Alzheimer's disease, Parkinson's disease, and lysosomal diseases affecting the central nervous system.

18. The method of claim 17, wherein said pharmaceutical composition is administered without the addition of phospholipid.

19. The method of treating diseases of the central nervous system according to claim 17, wherein the composition is administered orally, parenterally, mucosally, cutaneously, intrathecal or spinally.

20. The method of claim 17, wherein said methyl-β-cyclodextrin is the sole active ingredient of said pharmaceutical composition.

* * * * *